United States Patent [19]
Friese et al.

[11] Patent Number: 5,380,424
[45] Date of Patent: Jan. 10, 1995

[54] SENSOR WITH A CATALYTICALLY ACTIVE PROTECTIVE LAYER FOR DETERMINING THE OXYGEN CONTENT IN GASES, AND PROCESS FOR MANUFACTURING SUCH A SENSOR

[75] Inventors: Karl-Hermann Friese, Leonberg; Hans-Martin Wiedenmann, Stuttgart, both of Germany

[73] Assignee: Robert Bosch GmbH, Stuttgart, Germany

[21] Appl. No.: 81,325
[22] PCT Filed: Dec. 5, 1991
[86] PCT No.: PCT/DE91/00950
  § 371 Date: Jun. 24, 1993
  § 102(e) Date: Jun. 24, 1993
[87] PCT Pub. No.: WO92/12420
  PCT Pub. Date: Jul. 23, 1992

[30] Foreign Application Priority Data
  Jan. 4, 1991 [DE] Germany ............... 4100106

[51] Int. Cl.[6] .................................. G01N 27/26
[52] U.S. Cl. ........................ 204/429; 204/424; 204/426; 427/126.1; 427/126.2; 427/126.5; 427/383.5; 427/453; 427/454; 427/419.1; 427/419.2

[58] Field of Search ............... 204/421, 424, 428, 429, 204/426; 427/453, 454, 126.1, 126.2, 383.5, 419.1, 419.2, 126.5

[56] References Cited

U.S. PATENT DOCUMENTS
4,199,425  4/1980  Sinkevitch .................. 204/429
4,863,583  9/1989  Kurachi et al. .............. 204/429

FOREIGN PATENT DOCUMENTS
6063458  4/1985  Germany.

*Primary Examiner*—John Niebling
*Assistant Examiner*—Bruce F. Bell
*Attorney, Agent, or Firm*—Spencer, Frank & Schneider

[57] ABSTRACT

A sensor for determining the oxygen content in exhaust gases, particularly for lambda probes, is presented with catalytically active substances in the porous protective layer, which cover the electrode or electrodes exposed to the measuring gas, with discretely distributed platinum and homogenously distributed rhodium being used as catalytically active substances. The sensor in accordance with this invention guarantees excellent catalytic conversion of the exhaust gases and thus a control position of the sensor close to lambda=1.

20 Claims, 1 Drawing Sheet

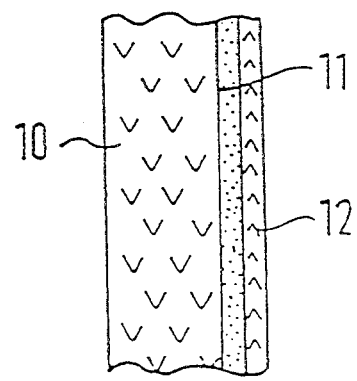

SENSOR WITH A CATALYTICALLY ACTIVE PROTECTIVE LAYER FOR DETERMINING THE OXYGEN CONTENT IN GASES, AND PROCESS FOR MANUFACTURING SUCH A SENSOR

BACKGROUND OF THE INVENTION

The invention relates to an electrochemical sensor for determining the oxygen content in gases, particularly in exhaust gases of internal combustion engines. A sensor of this general type is already known (DE-OS 37 37 215), and has a solid electrolytic body, at least one electrode on the side of the solid electrolytic body exposed to the measuring gas, as well as a protective layer with catalytically active substances on the electrode or electrodes exposed to the measuring gas, with the catalytically active substance being platinum or a platinum alloy. The incorporation of catalytically active substances into the porous protective layer which covers the electrode exposed to the measuring gas, is necessary in order to accelerate the setting of the thermodynamic equilibrium of the exhaust gas, and to achieve a control position as close as possible to $\lambda=1$. However, it has been shown that at low exhaust gas temperatures, platinum is not capable of catalysing the equilibrium setting to a satisfactory degree. On the other hand, rhodium demonstrates an excellent catalytic effect at low temperatures, in particular with regard to the reduction of nitric oxides. In the publication SAE Paper no. 880557 "Multi-Layered Zirconia Oxygen Sensor with Modified Rhodium Catalyst Electrode", a lamina-shaped oxygen probe is proposed which has a rhodium layer on a platinum electrode, with an insulating intermediate layer being provided, where appropriate, between the platinum and rhodium layers. Through this layer-type construction, the equilibrium setting in the exhaust gas, and thus also the probe characteristics, are improved. The platinum electrodes and the rhodium catalyst are applied in layers one on top of the other, by means of screen printing. Thus at least two operating steps are necessary, and the consumption of precious metals is relatively high. If the platinum or rhodium layers are applied directly one on top 8 the other, without a separating insulating layer, then in addition an alloy formation results, whereby a portion of the rhodium loses its catalytic effect. The raw material, rhodium is, however, more than five times more expensive than platinum, and the amount used should therefore be kept as low as possible.

SUMMARY OF THE INVENTION

In contrast, the sensor in accordance with this invention, and the process of its manufacture, have the advantage that very small amounts of material, in particular minimal amounts of rhodium, are employed in an optimum manner to improve the sensor control position, in particular at low temperatures. In particular, the present invention provides for an electrochemical sensor for determining the oxygen content in gases, particularly in exhaust gases of internal combustion engines. The sensor comprises a solid electrolyte composed of stabilized zirconium dioxide and/or other oxides which conduct oxygen ions, having at least one electrode on the side of the solid electrolyte exposed to the gas to be measured, and also having a porous ceramic protective layer on the electrode or electrodes exposed to the gas to be measured, containing active catalytic metals. One of the catalytic metals which is active at high temperatures is a discretely distributed component. This component is preferably platinum. The other active catalytic metal, which is active at low temperatures is a homogeneously distributed component. This component is preferably rhodium.

The sensor in accordance with this invention can, moreover, be manufactured in a manner which is simple from the point of view of production engineering.

For one thing, an adequate catalytic action at increased exhaust gas temperature is achieved through discrete distribution of the active components preferred at increased temperature, in particular platinum, into the porous protective layer, since at high temperatures, gas diffusion and catalytic reactions occur at an accelerated rate. For another thing, through the homogenous distribution of the components which are active at low temperatures, in particular rhodium, excellent catalytic effectiveness is achieved at low temperatures. Due to the distribution of the two catalytic metals in accordance with this invention, it is further guaranteed that the number of direct contact points between the two catalytic metals, and thus the undesirable alloy formation, is low.

In order to achieve the distribution of the catalytic metals in accordance with this invention, it has been shown to be particularly advantageous to add platinum, as a powder, and rhodium as an aqueous or organic solution of rhodium compounds, to the raw materials for forming the porous protective layer. For homogenous precipitation of extremely pure rhodium, an aqueous nitrate solution and an organic resinate solution have been shown to be particularly suitable.

The catalytic metals or the substances forming the catalytic metals can be mixed with the remaining raw materials forming the porous protective layer, e.g. aluminum oxides, magnesium spinel and/or zirconium dioxide, as well as, if appropriate, a bonding agent, a softener and/or a vehicle substance and applied to the previously manufactured electrode or electrodes in one operation e.g., by spraying, immersion or printing, followed by rescinerting. However, it is also possible to initially add just the platinum powder to the remaining raw materials and to complete the porous protective layer, and in one further operation, to impregnate the same with rhodium solutions and subsequently to release the rhodium through thermic treatment, preferably in a reducing or an inert atmosphere.

BRIEF DESCRIPTION OF THE DRAWINGS

The Figure shows a section of an electrochemical sensor according to the invention.

DESCRIPTION OF THE PREFERRED EMBODIMENTS

As shown in the figures, the solid electrolyte 10 carries the electrode 11 which is exposed to the gas to be measured, with this electrode 11 in turn being covered by the porous ceramic protective layer 12. In the protective layer 12, a component which is catalytically active at high temperature is distributed discretely, and a component which is catalytically active at low temperature is distributed homogenously.

The invention is described below on the basis of examples. The porous ceramic protective layer of the present invention preferably contains 0.5 to 5 percent by weight platinum and 0.05 to 0.5 percent by weight rhodium; and most preferably, contains 1 percent by weight platinum and 0.2 percent by weight rhodium. The sensor in accordance with this invention guarantees excellent catalytic conversion of the exhaust gases and thus a control position of the sensor close to $\lambda=1$.

EXAMPLE 1

A mixture of 65 parts by weight of ceramic material, consisting of 60 parts by weight of $-Al_2O_3$ powder (>99% $Al_2O_3$; specific surface 10 $m^2/g$) and 40 parts by weight of $ZrO_2$ powder (>99% $ZrO_2$; specific surface 1.5 $m^2/g$), 2 parts by weight of polyvinyl alcohol bonding agent, 1 part by weight of platinum powder (>99% platinum; specific surface 15 $m^2/g$), 0.4 parts by weight of rhodium nitrate (>99% Rh $(NO_3)_2$), the remainder water, is ground for 6 hours in a Vibratom mill.

The dispersion thus obtained is applied through spraying, in a layer density of about 200 $\mu m$, onto the portion of a solid electrolyte body equipped with an electrode layer. The sensor is then resintered for about 3 hours at a temperature in the region of 1400° C.

In this manner, a porous protective layer, with excellent catalytic activity at both high and low temperatures, is obtained over the electrode or electrodes exposed to the gas to be measured.

EXAMPLE 2

The following are ground together in a centrifugal ball mill:
60 parts by weight of an $Al_2O_3/ZrO_2$ mixed oxide powder, obtained by-co-precipitation, with 40 per cent by weight $ZrO_2$ with a specific surface of about 10 $m^2/g$,
5 parts by weight polyvinyl butyral as a bonding agent,
2.5 parts by weight dibutylphthalate as softener,
1 per cent by weight platinum powder (>99% platinum; specific surface 15 $m^2/g$),
1.5 per cent by weight rhodium resinate (17.8% rhodium), and
30 per cent by weight butylcarbitol as the vehicle.

The mixture is ground for 2 hours and subsequently applied by screen printing to the electrode or electrodes of an oxygen sensor of a familiar type. After drying, it is resintered for 2 hours at a temperature in the region of 1400° C.

EXAMPLE 3

By stirring for 15 minutes, a suspension is produced which consists of:
65 parts by weight of an $Al_2O_3/ZrO_2$ mixed oxide powder, as described in example 2,
1 part by weight of platinum powder (>99% platinum; specific surface 15 $m^2/g$),
0.2 per cent by weight rhodium resinate and
3.5 parts by weight of a vehicle system, consisting of 4.0 parts by weight terpineol, 60 parts by weight benzyl alcohol and 6 parts by weight ethyl cellulose.

The suspension is applied to the portion of a solid electrolyte sensor equipped with electrodes, by immersion or spraying, dried for half an hour at a temperature in the legion of 100° C., and subsequently resintered for 3 hours at a temperature in the region of 1400° C.

A porous protective layer with excellent catalytic characteristics at high and low temperatures is obtained.

EXAMPLE 4

The starting point of this process a suspension as described in example 3, but without the addition of the rhodium resinate. The suspension is applied to the electrodes, dried and resintered, as described in example 3. The finished protective layer is subsequently impregnated with an aqueous 10% rhodium nitrate solution, and baked for 1 hour at 900° C. in a reducing atmosphere. Again, a porous protective layer with excellent catalytic characteristics is obtained.

We claim:

1. An electrochemical sensor for determining the oxygen content in gas, comprising:
   (a) a solid electrolyte composed of an oxygen conducting material;
   (b) at least one electrode on the side of the solid electrolyte exposed to the gas to be measured;
   (c) a porous ceramic protective layer on said at least one electrode, said protective layer containing at least one catalytic metal which is active at high temperatures and which is discretely distributed therein, and at least one catalytic metal which is active at low temperatures which is homogeneously distributed therein, with said at least one catalytic metal active at high temperatures including platinum and said at least one catalytic metal active at low temperatures being rhodium.

2. The sensor of claim 1 wherein the solid electrolyte is stabilized zirconium dioxide, oxygen ion conducting oxides or mixtures of these oxides.

3. The sensor of claim 1 wherein the porous ceramic protective layer contains 0.5 to 5 percent by weight platinum.

4. The sensor of claim 3 wherein the porous ceramic protective layer contains 0.05 to 0.5 percent by weight rhodium.

5. The sensor of claim 1 wherein the porous ceramic protective layer contains 0.05 to 0.5 percent by weight rhodium.

6. The sensor of claim 1 wherein the porous ceramic protective layer contains 1 percent by weight platinum and 0.2 percent by weight rhodium.

7. A process for producing an electrochemical sensor for determining the oxygen content in a gas, comprising the steps of:
   (a) providing a solid electrolyte comprising stabilized zirconium dioxide, oxygen ion conducting oxides or mixtures of these oxides;
   (b) providing at least one electrode on a side of the solid electrolyte to be exposed to a gas to be measured;
   (c) forming a ceramic material mixture containing platinum, as a catalytic metal active at high temperatures, and rhodium, as a catalytic metal active at low temperatures, by mixing and grinding together platinum containing powder, ceramic raw materials and a liquid rhodium solution;
   (d) applying the ceramic material mixture as a protective layer to said at least one electrode; and
   (e) drying and sintering the ceramic material mixture of the protective layer whereby a porous ceramic protective layer is formed wherein the platinum is discretely distributed and the rhodium is homogeneously distributed.

8. The process of claim 7 wherein the liquid rhodium solution is an aqueous rhodium nitrate or a rhodium resinate solution.

9. The process of claim 7 wherein the ceramic raw material includes aluminum oxide, zirconium dioxide, magnesium spinel or a mixture of these substances.

10. The process of claim 7 wherein binders, solvents and softeners are additionally added to the mixture during said step of forming.

11. The process of claim 7 wherein said step of applying includes applying the ceramic material to the electrode by spraying, dipping or printing.

12. The process of claim 7 wherein the porous ceramic protective layer on the electrode is at least 150 micrometers thick subsequent to sintering.

13. The process of claim 7 wherein the platinum containing powder is platinum powder.

14. A process for producing an electrochemical sensor for determining the oxygen content in a gas, comprising the steps of:
   (a) providing a solid electrolyte comprising stabilized zirconium dioxide, oxygen ion conducting oxides or mixtures of these oxides;
   (b) providing at least one electrode on a side of the solid electrolyte to be exposed to a gas to be measured;
   (c) forming a ceramic material mixture by mixing and grinding together platinum containing powder and ceramic raw materials;
   (d) applying the ceramic material mixture as a protective layer on said at least one electrode;
   (e) drying and sintering the ceramic material of the protective layer to form a porous ceramic protective layer containing platinum as a catalytic metal active at high temperatures; and
   (f) thereafter, impregnating the platinum containing porous ceramic protective layer with a liquid rhodium solution and drying the impregnated layer, whereby a porous ceramic protective layer containing discretely distributed platinum as a catalytic metal which is active at high temperatures and homogeneously distributed rhodium as a catalytic metal which is active at low temperatures.

15. The process of claim 14 wherein the liquid rhodium solution is an aqueous rhodium nitrate or a rhodium resinate solution.

16. The process of claim 14 wherein the ceramic raw material is aluminum oxide, zirconium dioxide, magnesium spinel or a mixture of these substances.

17. The process of claim 14 wherein binders, solvents and softeners are additionally added to the mixture during said step of forming.

18. The process of claim 14 wherein said step of applying includes applying the ceramic material mixture to the at least one electrode by spraying, dipping or printing.

19. The process of claim 14 wherein the porous ceramic protective layer on the at least one electrode is at least 150 micrometers thick subsequent to sintering.

20. The process of claim 14 wherein the platinum containing powder is platinum powder.

* * * * *